United States Patent [19]

Manghisi et al.

[11] 3,933,803
[45] Jan. 20, 1976

[54] NEW BETA-AMINOKETONE DERIVATIVES

[75] Inventors: Elso Manghisi; Giuseppe Cascio; Liliana Bastianini, all of Milan, Italy

[73] Assignee: Instituto Luso Farmaco d'Italia S.r.l., Italy

[22] Filed: July 16, 1973

[21] Appl. No.: 379,812

[30] Foreign Application Priority Data

July 26, 1972  Italy................................ 27473/72

[52] U.S. Cl. ............ 260/240 G; 424/248; 424/251; 424/263; 424/267; 424/273; 424/275; 424/285; 424/321; 424/323; 424/326; 424/327; 260/240 A; 260/240 J; 260/247.5 R; 260/268 R; 260/293.72; 260/340.5; 260/552 SC; 260/554; 260/556 AR; 260/564 A; 269/564 F; 260/566 A
[51] Int. Cl.²................. C09B 23/00; C07C 97/10
[58] Field of Search...... 260/570.5 C, 240 A, 240 J, 260/240 G, 247.5 R, 268 R, 293.72, 340.5, 552 SC, 554, 556 AR, 564 A, 564 F, 566 A

[56] References Cited
UNITED STATES PATENTS 2,897,236  7/1959  Moss................................ 260/570.5

FOREIGN PATENTS OR APPLICATIONS 1,009,909  11/1965  United Kingdom.......... 260/247.5 R

OTHER PUBLICATIONS

Von Schonenberger et al., Arzn. Forschung, pp. 1082–1091 (1969).
Angeloni et al., Chem. Abstracts, Vol. 58, Col. 495 (a), 1963 (Abst. of Ateneo Parmense Vol. 33, pp. 219–225, (1962).
Cheronis et al., Semimicro Qualitative Organic Analysis, pp. 138, 242–250, Thomas Y. Crowell Co., NY, (1947).
Jacquier et al., Bull. Soc. Chim. France, 1956, pp. 1653–1666.
Smolanka, Chemical Abstracts Vol. 54, Col. 14186, (1960), (Abst. of Original Article).
Kozlov et al., Chemical Abstracts Vol. 70, Abst. No. 28787f, (1969).

*Primary Examiner*—John D. Randolph
*Attorney, Agent, or Firm*—Hill, Gross, Simpson, Van Santen, Steadman, Chiara & Simpson

[57] ABSTRACT

The invention relates to compounds of the formula:

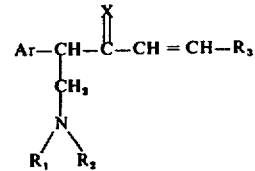

wherein Ar is a substituted or unsubstituted aryl group, $-N(R_1R_2)$ is a generic primary or secondary amine, X is O or a functional derivative of the C = O group, and $R_3$ is a generic hydrocarbyl radical. These compounds are endowed with anti-bacterial, anti-mitotic and anti-mycotic activity.

9 Claims, No Drawings

NEW BETA-AMINOKETONE DERIVATIVES

The present invention relates to a series of compounds of the general formula (I):

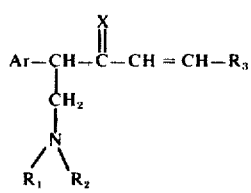

and their pharmaceutically acceptable salts with organic and inorganic acids, wherein (1) Ar represents an aryl group which may or may not be substituted with one or more halogen atoms, polyhalogenated alkyl groups, nitro groups, sulphonamide groups or hydroxyl, alkoxy, or methylenedioxy groups, (2)

represents the residue of a secondary amino group (such as methyl amino, ethyl amino, propyl amino, isopropyl amino, benzyl amino and phenethyl amino) or of a tertiary amino group (such as dimethyl amino, diethyl amino, diethanol amino and dibenzyl amino) or the residue of a heterocyclic amine (such as morpholine, pyrrolidine, piperidine or a 4,4-di-substituted piperidine, N-methyl piperazine, N-hydroxy-ethyl-piperazine, N-phenyl piperazine or N-o-methoxy-phenyl piperazine), (3) X represents an atom of oxygen or a functional derivative of a carbonyl group, such as the NOH, N—NH$_2$, N—NH—CO—NH$_2$,

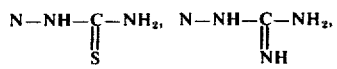

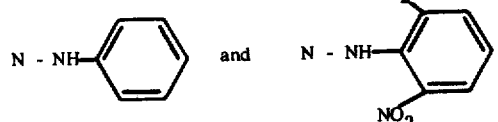

(4) R$_3$ represents a lower alkyl radical (such as methyl, ethyl or isopropyl), an aralkyl radical (such as benzyl or phenethyl), an aryl alkenyl radical (such as cinnamyl or furyl-vinyl), or an aryl radical (such as phenyl, tolyl, xylyl, chloro-phenyl, nitro-phenyl, hydroxy-phenyl, carboxy-phenyl, naphtyl, furyl, nitro-furyl, thienyl, pyrryl, pyridyl, imidazolyl and nitro-imidazolyl).

The invention also relates to processes for the preparation of compounds of the general formula (I). When X represents an atom of oxygen, they can be obtained by causing compounds of the general formula (II), $$Ar-CH-CO-CH_3$$
$$\quad\;\;|$$
$$\quad\;\;CH_2$$
$$\quad\;\;|$$
$$\quad\;\;N$$
$$\quad\;\;/\;\backslash$$
$$\quad R_1\;\;R_2$$

to react with the aldehydes of the general formula R$_3$—CHO, in which R$_3$ has the meaning given above, in the presence of basic catalysts, (such as hydrates of alkaline or alkaline-earth metals, metallic alcoholates, primary or secondary amines, or salts of organic acids) or acids (such as hydrohalic acids, sulphuric acid, phosphoric acid, acetic acid or acetic anhydride) in polar solvents (such as alcohol, hydro-alcoholic mixture, or acetic acid) or non-polar solvents (such as benzene or toluene) at a temperature ranging from −10°C. to the boiling point of the solvents.

The compounds having the general formula (II), $$Ar-CH-CO-CH_3$$
$$\quad\;\;|$$
$$\quad\;\;CH_2$$
$$\quad\;\;|$$
$$\quad\;\;N$$
$$\quad\;\;/\;\backslash$$
$$\quad R_1\;\;R_2$$

are obtained from the corresponding products of the formula Ar—CH$_2$—CO—CH$_3$ by Mannich condensation with formaldehyde and the respective amines $$HN{<}^{R_1}_{R_2}$$

When X represents the functional derivative of the carbonyl group, the products are obtained by the reaction of the ketones of formula (I) where X is oxygen, viz:

$$Ar-CH-\overset{\overset{X}{\|}}{C}-CH=CH-R_3$$
$$\quad\;\;|$$
$$\quad\;\;CH_2$$
$$\quad\;\;|$$
$$\quad\;\;N$$
$$\quad\;\;/\;\backslash$$
$$\quad R_1\;\;R_2$$

respectively, with, for example, hydroxyl amines, hydrazine, phenyl hydrazine, dinitro-phenyl hydrazine, semi-carbazide, thio-semi-carbazide or amino-guanidine by the methods usually described in literature for obtaining the said derivatives.

The products of the general formula (I), (the racemic products, the optically active forms and the geometrical isomers) are characterized by considerable antibacterial activity against gram-positive or gram-negative micro-organisms and by advantageous anti-mycotic activity over a wide range.

Their anti-mitotic activity is likewise considerable.

They can be administered orally, by injection or topically, by suitable pharmaceutical formulation, in a solid or liquid state or in the form of suspensions (for example, they can be provided in compressed form or as capsules, phials, syrups, suppositories, pomades and the like).

The following table summarizes some of the microbiological characteristics of various compounds described in the present application, the code numbers of which compounds have the meanings shown against them:

LR 389: 1-pyrrolidine-2,5-diphenyl-4-pentene-3-one chlorohydrate.
LR 399: 1-dimethyl-amine-2,5-diphenyl-4-pentene-3-one maleate.
LR 417: 1-pyrrolidine-2-phenyl-5-(2-furyl)-4-pentene-3-one maleate.
LR 418: 1-pyrrolidine-2-phenyl-5-styryl-4-pentene-3-one maleate.
LR 480: 1-pyrrolidine-2-phenyl-5-(2-thienyl)-4-pentene-3-one maleate.
LR 494: 1-pyrrolidine-2-phenyl-5-($\alpha$-naphthyl)-4-pentene-3-one chlorohydrate.

30 cc of alcohol, concentrated HCl is added while cooling until an acid pH is obtained. To the solution thus obtained are added 13.4 gr. of phenyl acetone and 4.5 gr. of paraformaldehyde and refluxed for 5 hours. After cooling the solvent is removed under reduced pressure. The residue crystallizes by the addition of acetone.

Melting point = 167° C. (from alcohol).

EXAMPLE 2

1-dimethyl-amino-2,5-diphenyl-4-pentene-3-one maleate.

To a solution, agitated and cooled to 5°–10° C. of 5.26 gr. of soda in tablets, 12 gr. of 1-dimethyl-amino-2-phenyl-butanone-(3)-chlorohydrate, in 50 cc of water and 70 cc of ethanol there is added 5.6 gr. of benzaldehyde all at the same time.

The mixture is kept agitated for 6 hours and diluted with 30 cc of water, the yellow solid being filtered off and washed several times with water.

Anti-microbic activity of a series of di B-amino ketones
Minimum Inhibiting Concentration In mcg/ml:

| | Micro-organisms | β-amino-ketones | | | | | |
|---|---|---|---|---|---|---|---|
| | | LR 389 | LR 399 | LR 417 | LR 418 | LR 480 | LR 494 |
| Gram+ | Staphylococcus aureus var. Oxford | 3.0 | 3.0 | 3.0 | 3.0 | 3.0 | 3.0 |
| | Staphylococcus aureus ATCC 6538 P | 1.5 | 1.5 | 1.5 | 1.5 | 3.0 | 1.5 |
| | Staphylococcus aureus 66/70 * | 3.0 | 3.0 | 3.0 | 3.0 | 3.0 | 3.0 |
| | Staphylococcus aureus 60/1 * | — | — | 3.0 | 3.0 | 3.0 | 1.5 |
| | Staphylococcus aureus Tour 3 B | 3.0 | 3.0 | 3.0 | 3.0 | 3.0 | 3.0 |
| | Staphylococus aureus Tour 10 B | 1.5 | 1.5 | 3.0 | 1.5 | 1.5 | 1.5 |
| | Straptococcus pyogenes A | 6.0 | 6.0 | 6.0 | 3.0 | 6.0 | 1.5 |
| | Straptococcus pyogenes A/203 | 1.5 | 1.5 | 1.5 | 1.5 | 3.0 | 1.5 |
| | Bacillus subtilis ATCC 6633 | 3.0 | 3.0 | 6.0 | 3.0 | 3.0 | 3.0 |
| | Sarcina lutea ATCC 9341 | — | — | — | 3.0 | 6.0 | 3.0 |
| Gram – | Escherichia coli 95 | 12 | 12 | 12 | >64 | 48 | >64 |
| | Escherichia coli 100 | 12 | 12 | 12 | >64 | 48 | >64 |
| | Escherichia coli 26/1 | >64 | >64 | >64 | >64 | >64 | >64 |
| | Escherichia coli K 12-10798 | — | — | >64 | >64 | >64 | >64 |
| | Escherichia coli K 69-1714 | >64 | >64 | >64 | >64 | >64 | >64 |
| | Proteus vulgaris | >64 | >64 | >64 | >64 | >64 | >64 |
| | Pseudomonas aeruginosa PG 72 | >64 | >64 | >64 | >64 | >64 | >64 |
| Mycetes | Candida albicans 966 P | 48 | 12 | 48 | >64 | >64 | >64 |
| | Aspergillus fumigatus ATCC 6285 | 12 | 12 | 48 | >64 | 48 | >64 |
| | Trichophyton mentagrophites ATCC 8757 | 6 | 3 | 6 | 12 | 6 | 6 |
| | Microsporum lanosum | — | — | — | 48 | 6 | 12 |
| | Penicillium chrysogenum istisan 152 | 3 | 3 | 12 | >64 | 12 | >64 |
| | Penicillium notatum N 97 | 12 | 12 | 24 | >64 | 24 | >64 |

* productive penicillinase

The invention is illustrate, but not limited, by the following examples.

The melting points are not corrected. The identity of the substances and their purity have been determined by elementary analyses of the C, H, N (and halogens, where present), infra-red spectra, N.M.R. and U.V.

EXAMPLE 1

1-pyrrolidine-2,5-diphenyl-4-pentene-3-one chlorohydrate.

To a solution, agitated and cooled to 5°–10° C. of 12 gr. of soda in tablets, 30 gr. of 1-pyrrolidine-2-phenyl-butanone-(3)-chlorohydrate, in 120 cc of water and 160 cc of ethanol, 12.6 gr. of benzaldehyde is added all at once.

The mixture is kept agitated for 4 hours and diluted with 50 cc of water, the yellow solid present then being filtered. The solid, washed with water and dried with a vacuum on $P_2O_5$ for a few hours, is dissolved in alcohol and converted into chlorohydrate with alcoholic HCl.

Melting point = 155° C. (from alcohol).

The 1-pyrrolidine-2-phenyl-butanone-(3)-chlorohydrate is prepared as follows: to 7.1 gr. of pyrrolidine in The solid is dried in a vacuum on $P_2O_5$ for 4 hours and then converted into the corresponding maleate.

Melting point = 101° C. (from alcohol).

The 1-dimethyl-amino-2-phenyl-butanone-(3)-chlorohydrate is prepared as follows: to 4.5 gr. of dimethyl amine in 30 cc of alcohol, concentrated HCl is added while cooling until an acid pH is obtained. To the solution thus obtained, 13.4 gr. of phenyl acetone and 4.5 gr. of paraformaldehyde are added, and refluxed for 5 hours. After cooling the solvent is removed under reduced pressure. The residue crystallizes by the addition of acetone.

Melting point = 151° C. (from alcohol).

EXAMPLE 3

1-pyrrolidine-2-phenyl-5-($\alpha$-naphthyl)-4-pentene-3-one-chlorohydrate.

A solution of 10 gr. of 1-pyrrolidine-2-phenyl-butanone-(3) and 6.1 gr. of $\alpha$-naphthaldehyde in 20 cc of acetic acid and 20 cc of acetic anhydride is refluxed for 4 hours.

The mixture is cooled and the solvent removed under reduced pressure. The residue is recovered with diluted HCl and extracted with diethyl ether. The separated aqueous phase is rendered alkaline with diluted soda in the cold and extracted with diethyl ether.

The organic phase, after washing several times with water and drying with $Na_2SO_4$ and finally evaporated to dryness, is converted into the corresponding chlorohydrate.

Melting point = 172° C. (from alcohol).

EXAMPLE 4

1-pyrrolidine-2-phenyl-5-styryl-4-pentene-3-one maleate.

To a solution, agitated and cooled to 5°–10° C. of 2 gr. of soda in tablets, 5 gr. of 1-pyrrolidine-2-phenyl-butanone-(3)-chlorohydrate in 20 cc of water and 30 cc of ethanol, there is added 2.65 gr. of cinnamic aldehyde all at the same time.

The mixture is kept agitated and cooled for 3 hours and then diluted with 20 cc of water the yellow solid present being filtered. The product is washed with water and dried in a vacuum over $P_2O_5$ for a few hours and then converted into the corresponding maleate.

Melting point = 118° C. (from alcohol).

EXAMPLE 5

1-pyrrolidine-2-phenyl-5-(2-thienyl)-4-pentene-3-one maleate.

To a solution, agitated and cooled to 5°–10° C. of 1.97 gr. of soda in tablets, 5 gr. of 1-pyrrolidine-2-phenyl-butanone-(3)-chlorohydrate in 19 cc of water and 26 cc of ethanol, there is added 2.2 gr. of 2-thiophenaldehyde all at the same time.

The mixture is kept agitated and cooled for 2 hours and the solid present is then filtered.

The product is washed several times with water and dried in a vacuum over $P_2O_5$, and finally converted into the corresponding maleate.

Melting point = 103-6° C. (from alcohol-ether).

EXAMPLE 6

1-pyrrolidine-2-phenyl-5-(2-furyl)-4-pentene-3-one maleate.

A solution of 15 gr. of 1-pyrrolidine-2-phenyl-butanone-(3), 2.2 gr. of 2-furane-aldehyde in 31 cc of $H_3PO_4$ at 65%, is kept stirred at 60° C. for 10 hours and then cooled.

The solution is then whipped with 200 cc of diethyl ether.

The separated aqueous phase is rendered alkaline in the cold, with soda at 20%, and then extracted with diethyl ether. The combined etheric extracts are washed with water until neutral, then dried on $Na_2SO_4$, filtered and evaporated to dryness at reduced pressure and at ambient temperature.

The residue is converted into the corresponding maleate.

Melting point = 112° C. (from alcohol).

EXAMPLE 7

1-pyrrolidine-2,5-diphenyl-4-pentene-3-one, oxime, chlorohydrate.

A solution of 3.7 gr. of 1-pyrrolidine-2,5-diphenyl-pentene-3-one chlorohydrate, 1.1 gr. of hydroxylamine chlorohydrate and 3 drops of concentrated hydrochloric acid in 50 cc of alcohol, is refluxed for 30 hours.

The solvent is then removed in a vacuum, after which the residual oil is recovered with acetone and filtered.

Melting point = 205° C. (from alcohol).

EXAMPLE 8

1-pyrrolidine-2,5-diphenyl-4-pentene-3-one, phenyl hydrazone, chlorohydrate.

A solution of 15 gr. of 1-pyrrolidine-2,5-diphenyl-4-pentene-3-one chlorohydrate, 5.2 gr. of phenyl hydrazine, and five drops of concentrated hydrochloric acid in 200 cc of alcohol, is refluxed for 27 hours and then filtered with animal charcoal.

The solvent is removed in a vacuum and the residue recrystallized.

Melting point = 190° C. (from alcohol).

As is apparent from the foregoing specification, the present invention is susceptible of being embodied with various alterations and modifications which may differ particularly from those that have been described in the preceeding specification and description. For this reason, it is to be fully understood that all of the foregoing is intended to be merely illustrative and is not to be construed or interpreted as being restrictive or otherwise limiting of the present invention, excepting as it is set forth and defined in the hereto-appendant claims.

What we claim is:

1. 5-substituted 1-amino-2-aryl-4-pentene-3-ones and the pharmaceutically acceptable salts thereof of the general formula (I):

$$Ar-CH-\overset{\overset{X}{\|}}{C}-CH=CH-R_3$$
$$\underset{\underset{R_1\ \ R_2}{\diagup\diagdown}}{\overset{\overset{CH}{|}}{\underset{N}{|}}}$$

wherein:

Ar represents an aryl radical which may be substituted with at least one member selected from the group consisting of halogen atoms, polyhalogenated alkyl radicals, nitro radicals, sulphonamide radicals, hydroxyl radicals, alkoxy radicals, methylene-dioxy radicals and mixtures thereof;

$$-N\diagdown\overset{R_1}{\underset{R_2}{\diagup}}$$

represents an amino radical selected from the group consisting of methyl amino, ethyl amino, propyl amino, isopropyl amino, benzyl amino, phenethyl amino, dimethyl amino, diethyl amino, diethanol amino, dibenzyl amino, morpholine, pyrrolidine, piperidine, 4,4-disubstituted piperidine, N-methyl piperazine, N-hydroxy ethyl piperazine, N-phenyl piperazine, and N-o-methoxy-phenyl piperazine;

X represents a member selected from the group consisting of an oxygen atom and a functional derivative of a carbonyl radical, selected from the group consisting of NOH, $N-NH_2$, $N-NH-CO-NH_2$, $$N-NH-\underset{S}{\overset{|}{C}}-NH_2, \quad N-NH-\underset{NH}{\overset{|}{C}}-NH_2,$$

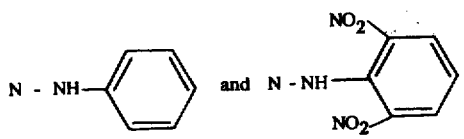

$R_3$ represents a radical selected from the group consisting of methyl, ethyl, isopropyl, benzyl, phenethyl, cinnamyl, furyl-vinyl, phenyl, tolyl, xylyl, chloro-phenyl, nitro-phenyl, hydroxyphenyl, carboxy-phenyl, naphthyl, furyl, nitro-furyl, thienyl, pyrryl, pyridyl, imidazolyl and nitroimidazolyl.

2. A 5-substituted 1-amino-2-aryl-4-pentene-3-one as defined in claim 1 wherein said compound comprises a 1-pyrrolidine-2,5-diphenyl-4-pentene-3-one and the pharmaceutically acceptable salts thereof with organic and inorganic acids.

3. A 5-substituted 1-amino-2-aryl-4-pentene-3-one as defined in claim 1 wherein said compound comprises a 1-dimethyl-amino-2,5-diphenyl-4-pentene-3-one and is pharmaceutically acceptable salts.

4. A 5-substituted 1-amino-2-aryl-4-pentene-3-one as defined in claim 1 wherein said compound comprises a 1-pyrrolidine-2-phenyl-5-(α-naphthyl)-4-pentene-3-one and its pharmaceutically acceptable salts with organic and inorganic acids.

5. A 5-substituted 1-amino-2-aryl-4-pentene-3-one as defined in claim 1 wherein said compound comprises a 1-pyrrolidine-2-phenyl-5-styryl-4-pentene-3-one and its pharmaceutically acceptable salts with organic and inorganic acids.

6. A 5-substituted 1-amino-2-aryl-4-pentene-3-one as defined in claim 1 wherein said compound comprises a 1-pyrrolidine-2-phenyl-5-(2-thienyl)-4-pentene-3-one and its pharmaceutically acceptable salts with organic and inorganic acids.

7. A 5-substituted 1-amino-2-aryl-4-pentene-3-one as defined in claim 1 wherein said compound comprises a 1-pyrrolidine-2-phenyl-5-(2-furyl)-4-pentene-3-one and its pharmaceutically acceptable salts with organic and inorganic acids.

8. A 5-substituted 1-amino-2-aryl-4-pentene-3-one as defined in claim 1 wherein said compound comprises a 1-pyrrolidine-2,5-diphenyl-4-pentene-3-one oxime and its pharmaceutically acceptable salts with organic and inorganic acids.

9. A 5-substituted 1-amino-2-aryl-4-pentene-3-one as defined in claim 1 wherein said compound comprises a 1-pyrrolidine-2,5-diphenyl-4-pentene-3-one phenyl hydrazone and its pharmaceutically acceptable salts with organic and inorgnic acids.

* * * * *